(12) United States Patent
Thastrup et al.

(10) Patent No.: US 6,172,188 B1
(45) Date of Patent: Jan. 9, 2001

(54) FLUORESCENT PROTEINS

(76) Inventors: Ole Thastrup, Birkevej 37, DK-3460 Bikerød; Søren Tullin, Solnavej 53, 1. tv., DK-2860-Søborg; Lars Kongsbak Poulsen, Vængestien 2A, DK-2840 Holte; Sara Petersen Bjørn, Klampenborgvej 102, DK-2800 Lyngby, all of (DK)

( * ) Notice: Under 35 U.S.C. 154(b), the term of this patent shall be extended for 0 days.

(21) Appl. No.: 08/819,612

(22) Filed: Mar. 17, 1997

Related U.S. Application Data

(63) Continuation of application No. PCT/DK96/00051, filed on Jan. 31, 1996.

(30) Foreign Application Priority Data

Sep. 22, 1995 (DK) .................................................. 1065/95

(51) Int. Cl.[7] .............................. C07K 1/00; C12P 21/06; C12N 5/00
(52) U.S. Cl. .................... 530/350; 530/808; 435/69.1; 435/325
(58) Field of Search .......................... 435/60, 325, 252.3, 435/254.11, 69.1, 40.5; 530/350, 808; 536/23.1

(56) References Cited

U.S. PATENT DOCUMENTS 5,610,031 * 3/1997 Burgesen et al. ................... 435/69.1

OTHER PUBLICATIONS

Delagrave et al (Bio/Technology, 19:151–154), 1995.*
Burgess et al (J. Cell Bio, 111:2129–2138), 1990.*
Lazar et al (Mol & Cell Biol. 8:1247–1252), 1988.*
Tao et al (J. Immunel, 143:2595–2601), 1989.*

* cited by examiner

*Primary Examiner*—Susan Ungar

(57) ABSTRACT

The present invention relates to novel variants of the fluorescent protein GFP having improved fluorescence properties.

15 Claims, 12 Drawing Sheets

DNA and Predicted primary amino acid sequence of GFP (Hind3-EcoR1 fragment).

5' - AAGCTTT

| ATG | AGT | AAA | GGA | GAA | GAA | CTT | TTC | ACT | GGA | GTT | GTC | CCA | ATT | CTT | GTT | GAA | TTA | GAT | CGC |
|-----|-----|-----|-----|-----|-----|-----|-----|-----|-----|-----|-----|-----|-----|-----|-----|-----|-----|-----|-----|
| MET | SER | LYS | GLY | GLU | GLU | LEU | PHE | THR | GLY | VAL | VAL | PRO | ILE | LEU | VAL | GLU | LEU | ASP | GLY |
| GAT | GTT | AAT | GGG | CAA | AAA | TTC | TCT | GTT | AGT | GGA | GAG | GGT | GAA | GGT | GAT | GCA | ACA | TAC | GGA |
| ASP | VAL | ASN | GLY | GLN | LYS | PHE | SER | VAL | SER | GLY | GLU | GLY | GLU | GLY | ASP | ALA | THR | TYR | GLY |
| AAA | CTT | ACC | CTT | AAA | TTT | ATT | TGC | ACT | ACT | GGG | AAG | CTA | CCT | GTT | CCA | TGG | CCA | ACG | CTT |
| LYS | LEU | THR | LEU | LYS | PHE | ILE | CYS | THR | THR | GLY | LYS | LEU | PRO | VAL | PRO | TRP | PRO | THR | LEU |
| GTC | ACT | ACT | TTC | TCT | TAT | GGT | GTT | CAA | TGC | TTT | TCA | AGA | TAC | CCA | GAT | CAT | ATG | AAA | CAG |
| VAL | THR | THR | PHE | SER | TYR | GLY | VAL | GLN | CYS | PHE | SER | ARG | TYR | PRO | ASP | HIS | MET | LYS | GLN |
| CAT | GAC | TTT | TTC | AAG | AGT | GCC | ATG | CCC | GAA | GGT | TAT | GTA | CAG | GAA | AGA | ACT | ATA | TTT | TAC |
| HIS | ASP | PHE | PHE | LYS | SER | ALA | MET | PRO | GLU | GLY | TYR | VAL | GLN | GLU | ARG | THR | ILE | PHE | TYR |
| AAA | GAT | GAC | GGG | AAC | TAC | AAG | ACA | CGT | GCT | GAA | GTC | AAG | TTT | GAA | GGT | GAT | ACC | CTT | GTT |
| LYS | ASP | ASP | GLY | ASN | TYR | LYS | THR | ARG | ALA | GLU | VAL | LYS | PHE | GLU | GLY | ASP | THR | LEU | VAL |
| AAT | AGA | ATC | GAG | TTA | AAA | GGT | ATT | GAT | TTT | AAA | GAA | GAT | GGA | AAC | ATT | CTT | GGA | CAC | AAA |
| ASN | ARG | ILE | GLU | LEU | LYS | GLY | ILE | ASP | PHE | LYS | GLU | ASP | GLY | ASN | ILE | LEU | GLY | HIS | LYS |
| ATG | GAA | TAC | AAT | TAT | AAC | TCA | CAC | AAT | GTA | TAC | ATC | ATG | GCA | GAC | AAA | CCA | AAG | AAT | GGA |
| MET | GLU | TYR | ASN | TYR | ASN | SER | HIS | ASN | VAL | TYR | ILE | MET | ALA | ASP | LYS | PRO | LYS | ASN | GLY |
| ATC | AAA | GTT | AAC | TTC | AAA | ATT | AGA | CAC | AAC | ATT | AAA | GAT | GGA | AGC | GTT | CAA | TTA | GCA | GAC |
| ILE | LYS | VAL | ASN | PHE | LYS | ILE | ARG | HIS | ASN | ILE | LYS | ASP | GLY | SER | VAL | GLN | LEU | ALA | ASP |
| CAT | TAT | CAA | CAA | AAT | ACT | CCA | ATT | GGC | GAT | GGC | CCT | GTC | CTT | TTA | CCA | GAC | AAC | CAT | TAC |
| HIS | TYR | GLN | GLN | ASN | THR | PRO | ILE | GLY | ASP | GLY | PRO | VAL | LEU | LEU | PRO | ASP | ASN | HIS | TYR |
| CTG | TCC | ACG | CAA | TCT | GCC | CTT | TCC | AAA | GAT | CCC | AAC | GAA | AAG | AGA | GAT | CAC | ATG | ATC | CTT |
| LEU | SER | THR | GLN | SER | ALA | LEU | SER | LYS | ASP | PRO | ASN | GLU | LYS | ARG | ASP | HIS | MET | ILE | LEU |
| CTT | GAG | TTT | GTA | ACA | GCT | GCT | GGG | ATT | ACA | CAT | GGC | ATG | GAT | GAA | CTA | TAC | AAA | TAA |     |
| LEU | GLU | PHE | VAL | THR | ALA | ALA | GLY | ILE | THR | HIS | GLY | MET | ASP | GLU | LEU | TYR | LYS |     |     |

ATGTCCAGACTTCCAATTGACACTAAAGGGATCCGAATTC – 3'

Fig. 2a

Nucleotide sequence (764bp) of GFP (Hind3-EcoR1 fragment)

AAGCTTTATGAGTAAAGGAGAAGAACTTTTCACTGGAGTT
GTCCCAATTCTTGTTGAATTAGATGGCGATGTTAATGGGC
AAAAATTCTCTGTTAGTGGAGAGGGTGAAGGTGATGCAAC
ATACGGAAAACTTACCCTTAAATTTATTTGCACTACTGGG
AAGCTACCTGTTCCATGGCCAACGCTTGTCACTACTTTCT
CTTATGGTGTTCAATGCTTTCAAGATACCCAGATCATAT
GAAACAGCATGACTTTTCAAGAGTGCCATGCCCGAAGGT
TATGTACAGGAAAGAACTATATTTTACAAAGATGACGGGA
ACTACAAGACACGTGCTGAAGTCAAGTTTGAAGGTGATAC
CCTTGTTAATAGAATCGAGTTAAAAGGTATTGATTTTAAA
GAAGATGGAAACATTCTTGGACACAAAATGGAATACAACT
ATAACTCACATAATGTATACATCATGGCAGACAAACCAAA
GAATGGCATCAAAGTTAACTTCAAAATTAGACACAACATT
AAAGATGGAAGCGTTCAATTAGCAGACCATTATCAACAAA
ATACTCCAATTGGCGATGGCCCTGTCCTTTTACCAGACAA
CCATTACCTGTCCACGCAATCTGCCCTTTCCAAAGATCCC
AACGAAAAGAGAGATCACATGATCCTTCTTGAGTTTGTAA
CAGCTGCTGGGATTACACATGGCATGGATGAACTATACAA
ATAAATGTCCAGACTTCCAATTGACACTAAAGGGATCCGA
ATTC

Fig. 2b

DNA and predicted primary amino acid sequence of F64L-Y66H-GFP (Hind3-EcoR1 fragment).

5' - AAGCTTT

| ATG | AGT | AAA | GGA | GAA | GAA | CTT | TTC | ACT | GGA | GTT | GTC | CCA | ATT | CTT | GTT | GAA | TTA | GAT | GGC |
|-----|-----|-----|-----|-----|-----|-----|-----|-----|-----|-----|-----|-----|-----|-----|-----|-----|-----|-----|-----|
| MET | SER | LYS | GLY | GLU | GLU | LEU | PHE | THR | GLY | VAL | VAL | PRO | ILE | LEU | VAL | GLU | LEU | ASP | GLY |
| GAT | GTT | AAT | GGG | CAA | AAA | TTC | TCC | GTT | AGT | GGA | GAG | GGT | GAA | GGT | GAT | GCA | ACA | TAC | GGA |
| ASP | VAL | ASN | GLY | GLN | LYS | PHE | SER | VAL | SER | GLY | GLU | GLY | GLU | GLY | ASP | ALA | THR | TYR | GLY |
| AAA | CTT | ACC | CTT | AAA | TTT | ATT | TGC | ACT | ACT | GGG | AAG | CTA | CCT | GTT | CCA | TGG | CCA | ACG | CTT |
| LYS | LEU | THR | LEU | LYS | PHE | ILE | CYS | THR | THR | GLY | LYS | LEU | PRO | VAL | PRO | TRP | PRO | THR | LEU |
| GTC | ACT | ACT | CTC | TCT | CAT | GGT | GTT | CAA | TGC | TTT | TCT | AGA | TAC | CCA | GAT | CAT | ATG | AAA | CAG |
| VAL | THR | THR | LEU | SER | HIS | GLY | VAL | GLN | CYS | PHE | SER | ARG | TYR | PRO | ASP | HIS | MET | LYS | GLN |
| CAT | GAC | TTT | TTC | AAG | AGT | GCC | ATG | CCC | GAA | GGT | TAT | GTA | CAG | GAA | AGA | ACT | ATA | TTT | TAC |
| HIS | ASP | PHE | PHE | LYS | SER | ALA | MET | PRO | GLU | GLY | TYR | VAL | GLN | GLU | ARG | THR | ILE | PHE | TYR |
| AAA | GAT | GAC | GGG | AAC | TAC | AAG | ACA | CGT | GCT | GAA | GTC | AAG | TTT | GAA | GGT | GAT | ACC | CTT | GTT |
| LYS | ASP | ASP | GLY | ASN | TYR | LYS | THR | ARG | ALA | GLU | VAL | LYS | PHE | GLU | GLY | ASP | THR | LEU | VAL |
| AAT | AGA | ATC | GAG | TTA | AAA | GGT | ATT | GAT | TTT | AAA | GAA | GAT | GGA | AAC | ATT | CTT | GGA | CAC | AAA |
| ASN | ARG | ILE | GLU | LEU | LYS | GLY | ILE | ASP | PHE | LYS | GLU | ASP | GLY | ASN | ILE | LEU | GLY | HIS | LYS |
| ATG | GAA | TAC | AAT | TAT | AAC | TCA | CAT | AAT | GTA | TAC | ATC | ATG | GCA | GAC | AAA | CCA | AAG | AAT | GGC |
| MET | GLU | TYR | ASN | TYR | ASN | SER | HIS | ASN | VAL | TYR | ILE | MET | ALA | ASP | LYS | PRO | LYS | ASN | GLY |
| ATC | AAA | GTT | AAC | TTC | AAA | ATT | AGA | CAC | AAC | ATT | AAA | GAT | GGA | AGC | GTT | CAA | TTA | GCA | GAC |
| ILE | LYS | VAL | ASN | PHE | LYS | ILE | ARG | HIS | ASN | ILE | LYS | ASP | GLY | SER | VAL | GLN | LEU | ALA | ASP |
| CAT | TAT | CAA | CAA | AAT | ACT | CCA | ATT | GGC | GAT | GGC | CCT | GTC | CTT | TTA | CCA | GAC | AAC | CAT | TAC |
| HIS | TYR | GLN | GLN | ASN | THR | PRO | ILE | GLY | ASP | GLY | PRO | VAL | LEU | LEU | PRO | ASP | ASN | HIS | TYR |
| CTG | TCC | ACG | CAA | TCT | GCC | CTT | TCC | AAA | GAT | CCC | AAC | GAA | AAG | AGA | GAT | CAC | ATG | ATC | CTT |
| LEU | SER | THR | GLN | SER | ALA | LEU | SER | LYS | ASP | PRO | ASN | GLU | LYS | ARG | ASP | HIS | MET | ILE | LEU |
| CTT | GAG | TTT | GTA | ACA | GCT | GCT | GGG | ATT | ACA | CAT | GGC | ATG | GAT | GAA | CTA | TAC | AAA | TAA | |
| LEU | GLU | PHE | VAL | THR | ALA | ALA | GLY | ILE | THR | HIS | GLY | MET | ASP | GLU | LEU | TYR | LYS | | |

ATGTCCAGACTTCCAATTGACACTAAAGGGATCCGAATTC – 3'

Fig. 3

DNA and predicted primary amino acid sequence of F64L-GFP (Hind3 – EcoR1 fragment).

```
5' - AAGCTTT
ATG AGT AAA GGA GAA GAA CTT TTC ACT GGA GTT GTC CCA ATT CTT GTT GAA TTA GAT GGC
MET SER LYS GLY GLU GLU LEU PHE THR GLY VAL VAL PRO ILE LEU VAL GLU LEU ASP GLY
GAT GTT AAT GGG CAA AAA TTC TCT GTT AGT GGA GAG GGT GAA GGT GAT GCA ACA TAC GGA
ASP VAL ASN GLY GLN LYS PHE SER VAL SER GLY GLU GLY GLU GLY ASP ALA THR TYR GLY
AAA CTT ACC CTT AAA TTT ATT TGC ACT ACT GGG AAG CTA CCT GTT CCA TGG CCA ACG CTT
LYS LEU THR LEU LYS PHE ILE CYS THR THR GLY LYS LEU PRO VAL PRO TRP PRO THR LEU
GTC ACT ACT CTC TCT TAT GGT GTT CAA TGC TTT TCT AGA TAC CCA GAT CAT ATG AAA CAG
VAL THR THR LEU SER TYR GLY VAL GLN CYS PHE SER ARG TYR PRO ASP HIS MET LYS GLN
CAT GAC TTT TTC AAG AGT GCC ATG CCC GAA GGT TAT GTA CAG GAA AGA ACT ATA TTT TAC
HIS ASP PHE PHE LYS SER ALA MET PRO GLU GLY TYR VAL GLN GLU ARG THR ILE PHE TYR
AAA GAT GAC GGG AAC TAC AAG ACA CGT GCT GAA GTC AAG TTT GAA GGT GAT ACC CTT GTT
LYS ASP ASP GLY ASN TYR LYS THR ARG ALA GLU VAL LYS PHE GLU GLY ASP THR LEU VAL
AAT AGA ATC GAG TTA AAA GGT ATT GAT TTT AAA GAA GAT GGA AAC ATT CTT GGA CAC AAA
ASN ARG ILE GLU LEU LYS GLY ILE ASP PHE LYS GLU ASP GLY ASN ILE LEU GLY HIS LYS
ATG GAA TAC AAT TAT AAC TCA CAT AAT GTA TAC ATC ATG GCA GAC AAA CCA AAG AAT GGC
MET GLU TYR ASN TYR ASN SER HIS ASN VAL TYR ILE MET ALA ASP LYS PRO LYS ASN GLY
ATC AAA GTT AAC TTC AAA ATT AGA CAC AAC ATT AAA GAT GGA AGC GTT CAA TTA GCA GAC
ILE LYS VAL ASN PHE LYS ILE ARG HIS ASN ILE LYS ASP GLY SER VAL GLN LEU ALA ASP
CAT TAT CAA CAA AAT ACT CCA ATT GGC GAT GGC CCT GTC CTT TTA CCA GAC AAC CAT TAC
HIS TYR GLN GLN ASN THR PRO ILE GLY ASP GLY PRO VAL LEU LEU PRO ASP ASN HIS TYR
CTG TCC ACG CAA TCT GCC CTT TCC AAA GAT CCC AAC GAA AAG AGA GAT CAC ATG ATC CTT
LEU SER THR GLN SER ALA LEU SER LYS ASP PRO ASN GLU LYS ARG ASP HIS MET ILE LEU
CTT GAG TTT GTA ACA GCT GCT GGG ATT ACA CAT GGC ATG GAT GAA CTA TAC AAA TAA
LEU GLU PHE VAL THR ALA ALA GLY ILE THR HIS GLY MET ASP GLU LEU TYR LYS
ATGTCCAGACTTCCAATTGACACTAAAGGGATCCGAATTC - 3'
```

Fig. 4

DNA and predicted primary amino acid sequence of F64L-S65T-GFP (Hind3 – EcoR1 fragment).

5' - AAGCTTT

| ATG | AGT | AAA | GGA | GAA | GAA | CTT | TTC | ACT | GGA | GTT | GTC | CCA | ATT | CTT | GTT | GAA | TTA | GAT | GGC |
|---|---|---|---|---|---|---|---|---|---|---|---|---|---|---|---|---|---|---|---|
| MET | SER | LYS | GLY | GLU | GLU | LEU | PHE | THR | GLY | VAL | VAL | PRO | ILE | LEU | VAL | GLU | LEU | ASP | GLY |
| GAT | GTT | AAT | GGG | CAA | AAA | TTC | TCT | GTT | AGT | GGA | GAG | GGT | GAA | GGT | GAT | GCA | ACA | TAC | GGA |
| ASP | VAL | ASN | GLY | GLN | LYS | PHE | SER | VAL | SER | GLY | GLU | GLY | GLU | GLY | ASP | ALA | THR | TYR | GLY |
| AAA | CTT | ACC | CTT | AAA | TTT | ATT | TGC | ACT | ACT | GGG | AAG | CTA | CCT | GTT | CCA | TGG | CCA | ACG | CTT |
| LYS | LEU | THR | LEU | LYS | PHE | ILE | CYS | THR | THR | GLY | LYS | LEU | PRO | VAL | PRO | TRP | PRO | THR | LEU |
| GTC | ACT | ACT | CTC | ACT | TAT | GGT | GTT | CAA | TGC | TTT | TCT | AGA | TAC | CCA | GAT | CAT | ATG | AAA | CAG |
| VAL | THR | THR | LEU | THR | TYR | GLY | VAL | GLN | CYS | PHE | SER | ARG | TYR | PRO | ASP | HIS | MET | LYS | GLN |
| CAT | GAC | TTT | TTC | AAG | AGT | GCC | ATG | CCC | GAA | GGT | TAT | GTA | CAG | GAA | AGA | ACT | ATA | TTT | TAC |
| HIS | ASP | PHE | PHE | LYS | SER | ALA | MET | PRO | GLU | GLY | TYR | VAL | GLN | GLU | ARG | THR | ILE | PHE | TYR |
| AAA | GAT | GAC | GGG | AAC | TAC | AAG | ACA | CGT | GCT | GAA | GTC | AAG | TTT | GAA | GGT | GAT | ACC | CTT | GTT |
| LYS | ASP | ASP | GLY | ASN | TYR | LYS | THR | ARG | ALA | GLU | VAL | LYS | PHE | GLU | GLY | ASP | THR | LEU | VAL |
| AAT | AGA | ATC | GAG | TTA | AAA | GGT | ATT | GAT | TTT | AAA | GAA | GAT | GGA | AAC | ATT | CTT | GGA | CAC | AAA |
| ASN | ARG | ILE | GLU | LEU | LYS | GLY | ILE | ASP | PHE | LYS | GLU | ASP | GLY | ASN | ILE | LEU | GLY | HIS | LYS |
| ATG | GAA | TAC | AAT | TAT | AAC | TCA | CAT | AAT | GTA | TAC | ATC | ATG | GCA | GAC | AAA | CCA | AAG | AAT | GGC |
| MET | GLU | TYR | ASN | TYR | ASN | SER | HIS | ASN | VAL | TYR | ILE | MET | ALA | ASP | LYS | PRO | LYS | ASN | GLY |
| ATC | AAA | GTT | AAC | TTC | AAA | ATT | AGA | CAC | AAC | ATT | AAA | GAT | GGA | AGC | GTT | CAA | TTA | GCA | GAC |
| ILE | LYS | VAL | ASN | PHE | LYS | ILE | ARG | HIS | ASN | ILE | LYS | ASP | GLY | SER | VAL | GLN | LEU | ALA | ASP |
| CAT | TAT | CAA | CAA | AAT | ACT | CCA | ATT | GGC | GAT | GGC | CCT | GTC | CTT | TTA | CCA | GAC | AAC | CAT | TAC |
| HIS | TYR | GLN | GLN | ASN | THR | PRO | ILE | GLY | ASP | GLY | PRO | VAL | LEU | LEU | PRO | ASP | ASN | HIS | TYR |
| CTG | TCC | ACG | CAA | TCT | GCC | CTT | TCC | AAA | GAT | CCC | AAC | GAA | AAG | AGA | GAT | CAC | ATG | ATC | CTT |
| LEU | SER | THR | GLN | SER | ALA | LEU | SER | LYS | ASP | PRO | ASN | GLU | LYS | ARG | ASP | HIS | MET | ILE | LEU |
| CTT | GAG | TTT | GTA | ACA | GCT | GCT | GGG | ATT | ACA | CAT | GGC | ATG | GAT | GAA | CTA | TAC | AAA | TAA | |
| LEU | GLU | PHE | VAL | THR | ALA | ALA | GLY | ILE | THR | HIS | GLY | MET | ASP | GLU | LEU | TYR | LYS | | |

ATGTCCAGACTTCCAATTGACACTAAAGGGATCCGAATTC – 3'

Fig. 5

FLUORESCENT PROTEINS

CROSS-REFERENCE TO RELATED APPLICATIONS

This application is a continuation of PCT/DK96/00051 filed Jan. 31, 1996, the contents of which is fully incorporated herein by reference, and claims priority of Danish application serial no. 1065/95 filed Sep. 22, 1995.

FIELD OF THE INVENTION

The present invention relates to novel variants of the fluorescent protein GFP having improved fluorescence properties.

BACKGROUND OF THE INVENTION

The discovery that Green Fluorescent Protein (GFP) from the jellyfish *A. victoria* retains its fluorescent properties when expressed in heterologous cells has provided biological research with a new, unique and powerful tool (Chalfie et al (1994). Science 263:802; Prasher (1995) Trends in Genetics 11:320; WO 95/07463).

Furthermore, the discovery of a blue fluorescent variant of GFP (Heim et al. (1994). Proc.Natl.Acad.Sci. 91:12501) has greatly increased the potential applications of using fluorescent recombinant probes to monitor cellular events or functions, since the availability of probes having different excitation and emission spectra permits simultaneous monitoring of more than one process.

However, the blue fluorescing variant described by Heim et al, Y66H-GFP, suffers from certain limitations: The blue fluorescence is weak (emission maximum at 448 nm), thus making detection difficult, and necessitating prolonged excitation of cells expressing Y66H-GFP. Moreover, the prolonged period of excitation is damaging to cells especially because the excitation wavelength is in the UV range, 360 nm–390 nm.

A very important aspect of using recombinant, fluorescent proteins in studying cellular functions is the non-invasive nature of the assay. This allows detection of cellular events in intact, living cells. A limitation with current fluorescent proteins is, however, that relatively high intensity light sources are needed for visualization. Especially with the blue variant, Y66H-GFP, it is necessary to excite with intensities that are damaging to most cells. It is worth mentioning that some cellular events like oscillations in intracellular signalling systems, e.g. cytosolic free calcium, are very photo sensitive. A further consequence of the low light emittance is that only high levels of expression can be detected. Obtaining such high level expression may stress the transcriptional and/or translational machinery of the cells.

The excitation spectrum of the green fluorescent protein from *Aequorea Victoria* shows two peaks: A major peak at 396 nm, which is in the potentially cell damaging UV range, and a lesser peak at 475 nm, which is in an excitation range that is much less harmful to cells. Heim et al.(1995), Nature, Vol. 373, p. 663–4, discloses a Ser65Thr mutation of GFP (S65T) having longer wavelengths of excitation and emission, 490 nm and 510 nm, respectively, than the wild-type GFP and wherein the fluorophore formation proceeded about fourfold more rapidly than in the wild-type GFP.

Expression of GFP or its fluorescent variants in living cells provides a valuable tool for studying cellular events and it is well known that many cells, including mammalian cells, are incubated at approximately 37° C. in order to secure optimal and/or physiologically relevant growth. Cell lines originating from different organisms or tissues may have different relevant temperatures ranging from about 35° C. for fibroblasts to about 38° C.–39° C. for mouse β-cells. Experience has shown, however, that the fluorescent signal from cells expressing GFP is weak or absent when said cells are incubated at temperatures above room temperature, cf. Webb, C. D. et al., Journal of Bacteriology, October 1995, p. 5906–5911. Ogawa H. et al., Proc. Natl. Acad. Sci. USA, Vol. 92, pp. 11899–11903, December 1995, and Lim et al. J. Biochem. 118, 13–17 (1995). The improved fluorescent variant S65T described by Heim et al. (1995) supra also displays very low fluorescence when incubated under normal culture conditions (37° C.), cf. Kaether and Gerdes FEBS Letters 369 (1995) pp. 267–271. Many experiments involving the study of cell metabolism are dependent on the possibility of incubating the cells at physiologically relevant temperatures, i.e. temperatures at about 37° C.

SUMMARY OF THE INVENTION

The purpose of the present invention is to provide novel fluorescent proteins, such as F64L-GFP, F64L-Y66H-GFP and F64L-S65T-GFP that result in a cellular fluorescence far exceeding the cellular fluorescence from cells expressing the parent proteins, i.e. GFP, the blue variant Y66H-GFP and the S65T-GFP variant, respectively. This greatly improves the usefulness of fluorescent proteins in studying cellular functions in living cells.

A further purpose of the invention is to provide novel fluorescent proteins that exhibit high fluorescence in cells expressing them when said cells are incubated at a temperature of 30° C. or above, preferably at a temperature of from 32° C. to 39° C., more preferably at a temperature of from 35° C. to 38° C., and most preferably at a temperature of about 37° C.

It is known that fluorescence in wild-type GFP is due to the presence of a chromophore, which is generated by cyclisation and oxidation of the SYG at position 65–67 in the predicted primary amino acid sequence and presumably by the same reasoning of the SHG sequence and other GFP analogues at positions 65–67, cf. Heim et al. (1994). Surprisingly, we have found that a mutation, preferably a substitution, of the F amino acid residue at position 1 preceding the S of the SYG or SHG chromophore or the T of the THG chromophore, in casu position 64 in the predicted primary amino acid sequence, results in a substantial increase of fluorescence intensity apparently without shifting the excitation and emission wavelengths. This increase is remarkable for the blue variant Y66H-GFP, which hitherto has not been useful in biological systems because of its weak fluorescence.

The F64L, F64I, F64V, F64A, and F64G substitutions are preferred, the F64L substitution being most preferred, but other mutations, e.g. deletions, insertions, or posttranslational modifications immediately preceding the chromophore are also included in the invention, provided that they result in improved fluorescence properties of the various fluorescent proteins. It should be noted that extensive deletions may result in loss of the fluorescent properties of GFP. It has been shown, that only one residue can be sacrificed from the amino terminus and less than 10 or 15 from the carboxyl terminus before fluorescence is lost, cf. Cubitt et al. TIBS Vol. 20 (11), pp. 448–456, November 1995.

Accordingly, one aspect of the present invention relates to a fluorescent protein derived from Aequorea Green Fluorescent Protein (GFP) or any functional analogue thereof, wherein the amino acid in position 1 upstream from the chromophore has been mutated to provide an increase of fluorescence intensity when the fluorescent protein of the invention is expressed in cells. Surprisingly, said mutation also results in a significant increase of the intensity of the fluorescent signal from cells expressing the mutated GFP and incubated at 30° C. or above 30° C., preferably at about 37° C., compared to the prior art GFP variants.

There are several advantages of the proteins of the invention, including:

Excitation with low energy light sources. Due to the high degree of brightness of F64L-Y66H-GFP and F64L-GFP their emitted light can be detected even after excitation with low energy light sources. Thereby it is possible to study cellular phenomena, such as oscillations in intracellular signalling systems, that are sensitive to light induced damage.

As the intensity of the emitted light from the novel blue and green emitting fluorescent proteins are of the same magnitude, it is possible to visualize them simultaneously using the same light source.

A real time reporter for gene expression in living cells is now possible, since the fluorescence from F64L-Y66H-GFP and F64L-GFP reaches a detectable level much faster than from wild type GFP, and prior known derivatives thereof. Hence, it is more suitable for real time studies of gene expression in living cells. Detectable fluorescence may be obtained faster due to shorter maturation time of the chromophore, higher emission intensity, or a more stable protein or a combination thereof.

Simultaneous expression of the novel fluorescent proteins under control of two or more separate promoters.

Expression of more than one gene can be monitored simultaneously without any damage to living cells.

Simultaneous expression of the novel proteins using one reporter as internal reference and the other as variable marker, since regulated expression of a gene can be monitored quantitatively by fusion of a promoter to e.g. F64L-GFP (or F64L-Y66HGFP), measuring the fluorescence, and normalizing it to the fluorescence of constitutively expressed F64L-Y66H-GFP (or F64L-GFP). The constitutively expressed F64L-Y66HGFP (or F64L-GFP) works as internal reference.

Use as a protein tag in living and fixed cells. Due to the strong fluorescence the novel proteins are suitable tags for proteins present at low concentrations. Since no substrate is needed and visualisation of the cells do not damage the cells dynamic analysis can be performed.

Use as an organelle tag. More than one organelle can be tagged and visualised simultaneously in living cells, e.g. the endoplasmic reticulum and the cytoskeleton.

Use as markers in cell or organelle fusions. By labelling two or more cells or organelles with the novel proteins, e.g. F64L-Y66H-GFP and F64L-GFP, respectively, fusions, such as heterokaryon formation, can be monitored.

Translocation of proteins fused to the novel proteins of the invention can be visualised. The translocation of intracellular proteins to a specific organelle, can be visualised by fusing the protein of interest to one fluorescent protein, e.g. F64L-Y66H-GFP, and labelling the organelle with another fluorescent protein, e.g. F64L-GFP, which emits light of a different wavelength. Translocation can then be detected as a spectral shift of the fluorescent proteins in the specific organelle.

Use as a secretion marker. By fusion of the novel proteins to a signal peptide or a peptide to be secreted, secretion may be followed on-line in living cells. A precondition for that is that the maturation of a detectable number of novel fluorescent protein molecules occurs faster than the secretion. This appears not to be the case for the fluorescent proteins GFP or Y66H-GFP of the prior art.

Use as genetic reporter or protein tag in transgenic animals. Due to the strong fluorescence of the novel proteins, they are suitable as tags for proteins and gene expression, since the signal to noise ratio is significantly improved over the prior art proteins, such as wild-type GFP.

Use as a cell or organelle integrity marker. By co-expressing two of the novel proteins, the one targeted to an organelle and the other expressed in the cytosol, it is possible to calculate the relative leakage of the cytosolic protein and use that as a measure of cell integrety.

Use as a marker for changes in cell morphology. Expression of the novel proteins in cells allows easy detection of changes in cell morphology, e.g. blebbing, caused by cytotoxic agents or apoptosis. Such morphological changes are difficult to visualize in intact cells without the use of fluorescent probes.

Use as a transfection marker, and as a marker to be used in combination with FACS sorting. Due to the increased brightness of the novel proteins the quality of cell detection and sorting can be significantly improved.

Use of the novel proteins as a ratio real-time kinase probe. By simultaneous expression of, e.g. F64L-GFP (or F64L-Y66H-GFP), which emits more light upon phophorylation and a derivative of F64L-Y66H-GFP which emits less light upon phophorylation. Thereby, the ratio of the two intensities would reveal kinase activity more accurately than only one probe.

Use as real-time probe working at near physiological concentrations. Since the novel proteins are significantly brighter than wild type GFP and prior art derivatives at about 37° C. the concentration needed for visualisation can be lowered. Target sites for enzymes engineered into the novel proteins, e.g. F64L-Y66H-GFP or F64L-GFP, can therefore be present in the cell at low concentrations in living cells. This is important for two reasons: 1) The probe must interfere as little as possible with the intracellular process being studied; 2) the translational and transcriptional apparatus should be stressed minimally.

The novel proteins can be used as real time probes based on energy transfer. A probe system based on energy transfer from, e.g. F64L-Y66H-GFP to F64L-GFP.

The novel proteins can be used as reporters to monitor live/dead biomass of organisms, such as fungi. By constitutive expression of F64L-Y66H-GFP or F64L-GFP in fungi the viable biomass will light up.

Transposon vector mutagenesis can be performed using the novel proteins as markers in transcriptional and translational fusions.

Transposons to be used in microorganisms encoding the novel proteins. The transposons may be constructed for translational and transcriptional fusions. To be used for screening for promoters.

Transposon vectors encoding the novel proteins, such as F64L-Y66H-GFP and F64L-GFP, can be used for tagging plasmids and chromosomes.

Use of the novel proteins enables the study of transfer of conjugative plasmids, since more than one parameter can be followed in living cells. The plasmid may be tagged by F64L-Y66H-GFP or F64L-GFP and the chromosome of the donor/recipient by F64L-Y66H-GFP or F64L-GFP.

Use as a reporter for bacterial detection by introducing the novel proteins into the genome of bacteriophages.

By engineering the novel proteins, e.g. F64L-Y66H-GFP or F64L-GFP, into the genome of a phage a diagnostic tool can be designed. F64L-Y66H-GFP or F64L-GFP will be expressed only upon transfection of the genome into a living host. The host specificity is defined by the bacteriophage.

Any novel feature or combination of features described herein is considered essential to this invention.

BRIEF DESCRIPTION OF THE DRAWINGS:

FIG. 2a is the DNA (SEQ ID No. 21) and predicted amino acid sequence (SEQ ID No. 22) of GFP;

FIG. 2b is the nucleotide sequence of GFP (SEQ ID No. 21);

FIG. 3 is the DNA (SEQ ID No. 15) and predicted amino acid sequence (SEQ ID No. 15) and predicted amino acid sequence of (SEQ ID NO. 16) of F64L-Y66HGFP;

FIG. 4 is the DNA (SEQ ID NO. 17) and predicted amino acid sequence (SEQ ID No. 18) of F64L-GFP;

FIG. 5 is the DNA (SEQ ID No. 19) and predicted amino acid sequence (SEQ ID No. 20) of F64L-S65T-GFP;

DETAILED DESCRIPTION OF THE INVENTION

Figure 1:
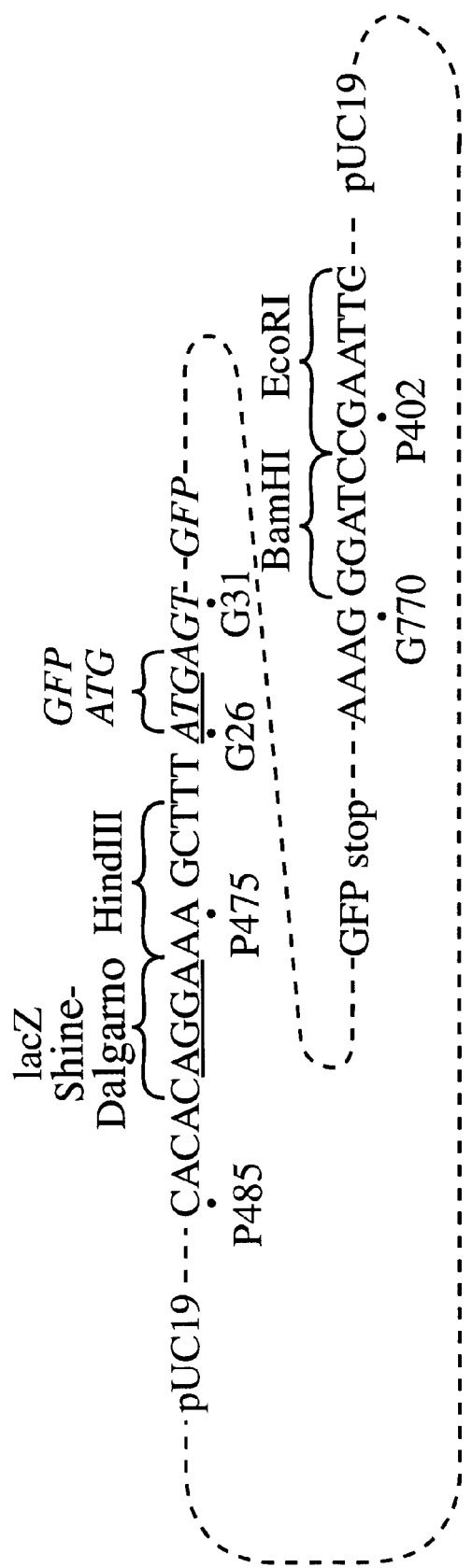
FIG. 1 shows a map of pUC 19-GFP plasmid construction.

In a preferred embodiment of the present invention, the novel fluorescent protein is the F64L mutant of GFP or the blue variant Y66H-GFP, said mutant showing increased fluorescence intensity. A preferred sequence of the gene encoding GFP derived from *Aequorea victoria* is disclosed in FIG. 2 herein. FIG. 2 shows the nucleotide sequence of a wild-type GFP (Hind3-EcoR1 fragment) and the amino acid sequence, wherein start codon ATG corresponds to position 8 and stop codon TAA corresponds to position 722 in the nucleotide sequence. A microorganism, *E. coli* NN049087, carrying the DNA sequence shown in FIG. 2 has been deposited for the purpose of patent procedure according to the Budapest Treaty in Deutsche Sammlung von Mikroorganismen und Zellkylturen GmbH, Mascheroderweg 1 b, D-38124 Braunschweig, Federal Republic of Germany, under the deposition No. DSM 10260. Another sequence of an isotype of this gene is disclosed by Prasher et al., *Gene* 111, 1992, pp. 229–233 (GenBank Accession No. M62653). Besides, the novel fluorescent proteins may also be derived from other fluorescent proteins, e.g. the fluorescent protein of the sea pansy *Renilla reniformis*.

Herein the abbreviations used for the amino acids are those stated in J. Biol. Chem. 243 (1968), 3558.

The DNA construct of the invention encoding the novel fluorescent proteins may be prepared synthetically by established standard methods, e.g. the phosphoamidite method described by Beaucage and Caruthers, *Tetrahedron Letters* 22 (1981), 1859–1869, or the method described by Matthes et al., *EMBO Journal* 3 (1984), 801–805. According to the phosphoamidite method, oligonucleotides are synthesized, e.g. in an automatic DNA synthesizer, purified, annealed, ligated and cloned in suitable vectors.

The DNA construct may also be prepared by polymerase chain reaction (PCR) using specific primers, for instance as described in U.S. Pat. No. 4,683,202 or Saiki et al., *Science* 239 (1988), 487–491. A more recent review of PCR methods may be found in *PCR Protocols,* 1990, Academic Press, San Diego, Calif., USA.

The DNA construct of the invention may be inserted into a recombinant vector which may be any vector which may conveniently be subjected to recombinant DNA procedures. The choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the fluorescent protein of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the fluorescent protein of the invention.

The promoter may be any DNA sequence which shows transcriptional activity in the host cell of choice and may be derived from genes encoding proteins either homologous or heterologous to the host cell, including native Aequorea GFP genes.

Examples of suitable promoters for directing the transcription of the DNA sequence encoding the fluorescent protein of the invention in mammalian cells are the SV40 promoter (Subramani et al., *Mol. Cell Biol.* 1 (1981), 854–864), the MT-1 (metallothionein gene) promoter (Palmiter et al., *Science* 222 (1983), 809–814) or the adenovirus 2 major late promoter.

An example of a suitable promoter for use in insect cells is the polyhedrin promoter (U.S. Pat. No. 4,745,051; Vasuvedan et al., *FEBS Lett.* 311, (1992) 7–11), the P10 promoter (J. M. Vlak et al., *J. Gen. Virology* 69, 1988, pp. 765–776), the *Autographa californica* polyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

Examples of suitable promoters for use in yeast host cells include promoters from yeast glycolytic genes (Hitzeman et al., *J. Biol. Chem.* 255 (1980), 12073–12080; Alber and Kawasaki, *J. Mol. Appl. Gen.* 1 (1982), 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304 (1983), 652–654) promoters.

Examples of suitable promoters for use in filamentous fungus host cells are, for instance, the ADH3 promoter (McKnight et al., *The EMBO J.* 4 (1985), 2093–2099) or the tpiA promoter. Examples of other useful promoters are those derived from the gene encoding *A. oryzae* TAKA amylase, *Rhizomucor miehei* aspartic proteinase, A. niger neutral α-amylase, A. niger acid stable α-amylase, A. niger or A. awamori glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

Examples of suitable promoters for use in bacterial host cells include the promoter of the *Bacillus stearothermophilus* maltogenic amylase gene, the Bacillus licheniformis alpha-amylase gene, the *Bacillus amyloliquefaciens* BAN amylase gene, the *Bacillus subtilis* alkaline protease gene, or the *Bacillus pumilus* xylosidase gene, or by the phage Lambda $P_R$ or $P_L$ promoters or the *E. coli* lac, trp or tac promoters.

The DNA sequence encoding the novel fluorescent proteins of the invention may also, if necessary, be operably connected to a suitable terminator, such as the human growth hormone terminator (Palmiter et al., op. cit.) or (for fungal hosts) the TPI1 (Alber and Kawasaki, op. cit. or ADH3 (McKnight et al., op. cit.) terminators. The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

The recombinant vector may further comprise a DNA sequence enabling the vector to replicate in the host cell in question. An example of such a sequence (when the host cell is a mammalian cell) is the SV40 origin of replication.

When the host cell is a yeast cell, suitable sequences enabling the vector to replicate are the yeast plasmid 2µ replication genes REP 1–3 and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125–130), or one which confers resistance to a drug, e.g. ampicillin, kanamycin, tetracyclin, chloramphenicol, neomycin or hygromycin. For filamentous fungi, selectable markers include amdS, pyrG, argB, niaD, sC.

The procedures used to ligate the DNA sequences coding for the fluorescent protein of the invention, the promoter and optionally the terminator and/or secretory signal sequence, respectively, and to insert them into suitable vectors containing the information necessary for replication, are well known to persons skilled in the art (cf., for instance, Sambrook et al., op. cit.).

The host cell into which the DNA construct or the recombinant vector of the invention is introduced may be any cell which is capable of expressing the present DNA construct and includes bacteria, yeast, fungi and higher eukaryotic cells.

Examples of bacterial host cells which, on cultivation, are capable of expressing the DNA construct of the invention are grampositive bacteria, e.g. strains of Bacillus, such as *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis*, or strains of Streptomyces, such as *S. lividans* or *S. murinus*, or gramnegative bacteria such as *Echerichia coli*. The transformation of the bacteria may be effected by protoplast transformation or by using competent cells in a manner known per se (cf. Sambrook et al., supra).

Examples of suitable mammalian cell lines are the HEK293 and the HeLa cell lines, primary cells, and the COS (e.g. ATCC CRL 1650), BHK (e.g. ATCC CRL 1632, ATCC CCL 10), CHL (e.g. ATCC CCL39) or CHO (e.g. ATCC CCL 61) cell lines. Methods of transfecting mammalian cells and expressing DNA sequences introduced in the cells are described in e.g. Kaufman and Sharp, *J. Mol. Biol.* 159 (1982), 601–621; Southern and Berg, *J. Mol. Appl. Genet.* 1 (1982), 327–341; Loyter et al., *Proc. Natl. Acad. Sci. USA* 79 (1982), 422–426; Wigler et al., *Cell* 14 (1978), 725; Corsaro and Pearson, *Somatic Cell Genetics* 7 (1981), 603, Graham and van der Eb, *Virology* 52 (1973), 456; and Neumann et al., *EMBO J.* 1 (1982), 841–845.

Examples of suitable yeast cells include cells of Saccharomyces spp. or Schizosaccharomyces spp., in particular strains of *Saccharomyces cerevisiae* or *Saccharomyces kluyveri*. Methods for transforming yeast cells with heterologous DNA and producing heterologous polypeptides therefrom are described, e.g. in U.S. Pat. No. 4,599,311, U.S. Pat. No. 4,931,373, U.S. Pat. Nos. 4,870,008, 5,037,743, and U.S. Pat. No. 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the fluorescent protein of the invention may be preceded by a signal sequence and optionally a leader sequence, e.g. as described above. Further examples of suitable yeast cells are strains of Kluyveromyces, such as *K. lactis*, Hansenula, e.g. *H. polymorpha*, or Pichia, e.g. *P. pastoris* (cf. Gleeson et al., *J. Gen. Microbiol.* 132, 1986, pp. 3459–3465; U.S. Pat. No. 4,882,279).

Examples of other fungal cells are cells of filamentous fungi, e.g. Aspergillus spp., Neurospora spp., Fusarium spp. or Trichoderma spp., in particular strains of *A. oryzae, A. nidulans* or *A. niger*. The use of Aspergillus spp. for the expression of proteins is described in, e.g., EP 272 277, EP 230 023, EP 184 438.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. No. 4,745,051; U.S. Pat. No. 4,879,236; U.S. Pat. Nos. 5,155,037; 5,162,222; EP 397,485) all of which are incorporated herein by reference. The insect cell line used as the host may suitably be a Lepidoptera cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting the expression of the present DNA construct after which the cells may be used in the screening method of the invention. Alternatively, the cells may be disrupted after which cell extracts and/or supernatants may be analysed for fluorescence.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection).

In the method of the invention, the fluorescence of cells transformed or transfected with the DNA construct of the invention may suitably be measured in a spectrometer or a fluorescence microscope where the spectral properties of the cells in liquid culture may be determined as scans of light excitation and emission.

The invention is further illustrated in the following examples with reference to the appended drawings.

EXAMPLE 1

Cloning of cDNA encoding GFP

Briefly, total RNA, isolated from *A. Victoria* by a standard procedure (Sambrook et al., Molecular Cloning. 2., eds. (1989) (Cold Spring Harbor Laboratory Press: Cold Spring Harbor, N.Y.), 7.19–7.22) was converted into cDNA by using the AMV reverse transcriptase (Promega, Madison, Wis., USA) as recommended by the manufacturer. The cDNA was then PCR amplified, using PCR primers designed on the basis of a previously published GFP sequence (Prasher et al., Gene 111 (1992), 229–233; GenBank accession No. M62653) together with the UlTma™ polymerase (Perkin Elmer, Foster City, Calif., USA). The sequences of the primers were: GFP-2: TGGAATAAGCTT-TATGAGTAAAGGAGAAGAACTTTT (SEQ ID NO: 1) and GFP-1: AAGAATTCGGATCCCTTTAGTGTCAAT-TGGAAGTCT (SEQ ID NO:2)

Restriction endonuclease sites inserted in the 5' (a HindIII site) and 3' (EcoRI and BamHI sites) primers facilitated the cloning of the PCR amplified GFP cDNA into a slightly modified pUC19 vector. The details of the construction are as follows: LacZ Shine-Dalgarno AGGA, immediately followed by the 5' HindIII site plus an extra T and the GFP ATG codon, giving the following DNA sequence at the lacZ-promoter GFP fusion point: $P_{LacZ}$-AGGAAAGCTTTATG-GFP. At the 3' end of the GFP cDNA, the base pair corresponding to nucleotide 770 in the published GFP sequence (GenBank accession No. M62653) was fused to the EcoR1 site of the pUC19 multiple cloning site (MCS) through a PCR generated BamHI, EcoRI linker region).

The DNA sequence and predicted primary amino acid sequence of GFP is shown below in FIG. 2*a*. Another DNA sequence encoding the same amino acid sequence as shown in FIG. 2*a* is shown in FIG. 2*b*. To generate the blue fluorescent variant described by Heim et al. (1994), a PCR primer incorporating the Y66H substitution responsible for changing green fluorescence into blue fluorescence was used as 5' PCR primer in combination with a GFP specific 3' primer. The template was the GFP clone described above. The sequence of the 5' primer is 5'-CTACCTGTTCCATG GCCAACGCTTGTCACTACTTTCCTCATGGT GTTCAATGCTT TTCTAGATACCC-3' (SEQ ID NO:3). Its 5' end corresponds to position 164 in the GFP sequence. In addition to the Y66H substitution, the 5' primer introduces a A to T change at position 223; this mutation creates a Xba1 site without changing an amino acid. The 5' primer also contains the naturally occuring Nco1 recognition sequence (position 173 in the GFP sequence). The sequence of the 3' primer is 5'-AAGAATTCGGATCCCTTTAGTGTCAATT GGAAGTCT-3' (SEQ ID NO:4). Position 3 from the 5' end is the first base of the EcoR1 recognition site that corresponds to the 3' end of the GFP sequence. The resulting PCR product was digested with Nco1 and EcoR1 and cloned into an Nco1-EcoR1 vector fragment to reconstitute the entire Y66H25 GFP gene.

*E. coli* cells carrying an expression vector containing Y66H-GFP were grown overnight in the presence of 10 micrograms per ml N-methyl-N-nitro-N-nitrosoguanidine. Plasmid DNA was isolated, the 764 bp Hind3-EcoR1 insert containing Y66H-GFP was isolated and cloned into a Hind3-EcoR1 digested vector fragment, allowing expression of the insert in *E. coli*. *E. coli* transformants were inspected for blue fluorescence when excited with a 365 nm UV light, and colonies that appeared to fluoresce stronger than wildtype BFP were identified.

10 ng DNA from one particular colony was used as template in a PCR reaction containing 1.5 units of Taq polymerase (Perkin Elmer), 0.1 mM $MnCl_2$, 0.2 mM each of dGTP, dCTP and dTTP, 0.05 mM dATP, 1.7 mM $MgCl_2$ and the buffer recommended by the manufacturer. The primers used flank the Y66H-GFP insert. The sequence of the 5' primer was 5'-AATTGGTACCAAGGAGGTAAGCT TTATGAG-3' (SEQ ID NO:5); it contains a Hind3 recognition sequence. The sequence of the 3' primer was 5-CTTTCGTTTTGAATTCGGATCCCTTTAGTG-3' (SEQ ID NO:6); it contains a EcoR1 recognition sequence.

The PCR product was digested with Hind3 and EcoR1 and cloned into a Hind3EcoR1 digested vector fragment, allowing expression of the insert in *E.coli*. *E.coli* transformants were inspected for blue fluorescence when excited with a 365 nm UV light, and colonies that appeared to fluoresce stronger than Y66H-GFP were identified. Plasmid DNA from one strongly fluorescing colony (called BX12-1A) was isolated and the Y66H-GFP insert was subjected to sequence determination. The mutation F64L was identified. This mutation replaces the phenylalanine residue preceding the SHG tripeptide chromophore sequence of Y66H-GFP with leucine. No other aminoacid changes were present in the Y66H-GFP sequence of BX12-1A. The DNA sequence and predicted primary amino acid sequence of F64L-Y66H-GFP is shown in FIG. 3 below.

EXAMPLE 2

F64L-GFP was constructed as follows: An *E.coli* expression vector containing Y66H-GFP was digested with restriction enzymes Nco1 and Xba1. The recognition sequence of Nco1 is located at position 173 and the recognition sequence of Xba1 is located at position 221 in the F64L-Y66H-GFP sequence listed below. The large Nco1-Xba1 vector fragment was isolated and ligated with a synthetic Nco1-Xba1 DNA linker of the following sequence:

One DNA strand has the sequence:
5'-CATGGCCAACGCTTGTCACTACTCTCTTATG
GTGTTCAATGCTTTT-3' (SEQ ID NO:7)

The other DNA strand has the sequence:
5'-CTAGAAAAGCATTGAACACCATAAGAGAGAG
TAGTGACAAGCGTTGGC-3' (SEQ ID NO:8)

Upon annealing, the two strands form a Nco1-Xba1 fragment that incorporates the sequence of the GFP chromophore SYG with the F64L substitution preceding SYG. The DNA sequence and predicted primary amino acid sequence of F64L-GFP is shown in FIG. 4 below.

The S65T-GFP mutation was described by Heim et al (Nature vol.373 pp. 663–664, 1995). F64L-S65T-GFP was constructed as follows: An *E.coli* expression vector containing Y66H-GFP was digested with restriction enzymes Nco1 and Xba1. The recognition sequence of Nco1 is located at position 173 and the recognition sequence of Xba1 is located at position 221 in the F64L-Y66H-GFP sequence listed below. The large Nco1-Xba1 vector fragment was isolated and ligated with a synthetic Nco1-Xba1 DNA linker of the following sequence:

One DNA strand has the sequence:
5'-CATGGCCAACGCTTGTCACTACTCTCACTTATG
GTGTTCAATGCTTTT-3' (SEQ ID NO:9)

The other DNA strand has the sequence:
5'-CTAGAAAAGCATTGAACACCATAAGTGAGAGT
AGTGACAAGCGTTGGC-3' (SEQ ID NO: 10).

Upon annealing, the two strands form a Nco1-Xba1 fragment that incorporates the F64L and S65T mutations in the GFP chromophore. The DNA sequence and predicted primary amino acid sequence of F64L-S65T-GFP is shown in FIG. 5 below.

The *E. coli* expression vector contains an IPTG (isopropyl-thio-galactoside)-inducible promoter. The *E. coli* strain used is a del(lacZ)MI5 derivative of K 803 (Sambrook et al. supra).

The GFP allele present in the pGFP-N1 plasmid (available from Clontech Laboratories) was introduced into the IPTG inducible *E.coli* expression vector in the following manner:

1 ng pGFP-N1 plasmid DNA was used as template in a standard PCR reaction where the 5' PCR primer had the sequence:
5'-TGGAATAAGCTTTATGAGTAAAGGAGAAGAACT
TTT-3' (SEQ ID NO: 11) and the 3' PCR primer had the sequence:
5'-GAATCGTAGATCTTTATTTGTATAGTTCATCCATG-3' (SEQ ID NO: 12).

The primers flank the GFP-N 1 insert in the vector pGFP-N1. The 5' primer includes the ATG start codon preceded by a Hind3 cloning site. The 3' primer includes a TAA stop codon followed by a Bgl2 cloning site.

The PCR product was digested with Hind3 and Bgl2 and cloned into a Hind35 BamHIdigested vector fragment behind an IPTG inducible promoter, allowing expression of the insert in *E.coli* in the presence of IPTG.

The lacZ gene present in the pZeoSV-LacZ plasmid (available from Invitrogen) was introduced into the IPTG inducible *E.coli* expression vector in the following manner:

1 ng pZeoSV-LacZ plasmid DNA was used as template in a standard PCR reaction where the 5' PCR primer had the sequence:
5'-TGGAATAAGCTTTATGGATCCCGTCGTTTTACAA
CGTCGT-3' (SEQ ID NO: 13) and the 3' PCR primer had the sequence:
5'-GCGCGAATTCTTATTATTATTTTTGACACCAGAC-3' (SEQ ID NO: 14).

The primers flank the lacZ insert in the vector pZeoSV-LacZ. The 5' primer includes the ATG start codon preceded by a Hind3 cloning site. The 3' primer includes a TAA stop codon followed by an EcoR1 cloning site.

The PCR product was digested with Hind3 and EcoR1 and cloned into a Hind3-EcoR1 digested vector fragment behind an IPTG inducible promoter, allowing expression of the insert in *E.coli* in the presence of IPTG.

To measure and compare the fluorescence generated in *E. coli* cells expressing GFP, GFP-N1, F64L-GFP, F64L-S65T-GFP, Y66H-GFP, F64L-Y66H-GFP or beta-galactosidase (as background control) under various conditions the following experiments were done:

*E. coli* cells containing an expression plasmid allowing expression of one of the various gene products upon induction with IPTG were grown in LB medium containing 100 micrograms per milliliter ampicillin and no IPTG. To 1 ml cell suspension was added 0.5 ml 50% glycerol and cells were frozen and kept frozen at −80 C.

Cells from the −80 C glycerol stocks were inoculated into 2 ml LB medium containing 100 µg/ml ampicillin and grown with aeration at 37 C for 6 hours. 2 microliters of this inoculum was transferred to each of two tubes containing 2 ml of LB medium with 100 µg/ml ampicillin and 1 mM IPTG. The two sets of tubes were incubated with aeration at two different temperatures: room temperature (22 C) and 37 C.

After 16 hours 0.2 ml samples were taken of cells expressing GFP, GFP-N1, F64L-GFP, F64L-S65T-GFP, Y66H-GFP, F64L-Y66H-GFP or beta-galactosidase. Cells were pelleted, the supernatant was removed, cells were resuspended in 2 ml water and transferred to a cuvette. Fluorescence emission spectra were measured in a LS-50 luminometer (Perkin-Elmer) with excitation and emission slits set to 10 nm. The excitation wavelengths were set to 398 nm and 470 nm for GFP, GFP-N1, F64L-GFP and F64L-S65T-GFP; 398 nm is near the optimal excitation wavelength for GFP, GFP-N1 and F64L-GFP, and 470 nm is near the optimal excitation wavelength for F64L-S65T-GFP. For Y66H-GFP and F64L-Y66H-GFP the excitation wavelength was set to 380 nm, which is near the optimal excitation wavelength for these derivatives. Beta-galactosidase expressing cells were included as background controls. Following the measurements in the LS-50 luminometer, the optical density at 450 nm was measured for each sample in a spectrophotometer (Lambda UV/VIS, Perkin-Elmer). This is a measure of total cells in the assay. Luminometer data were normalized to the optical density of the sample.

Figure 6A:
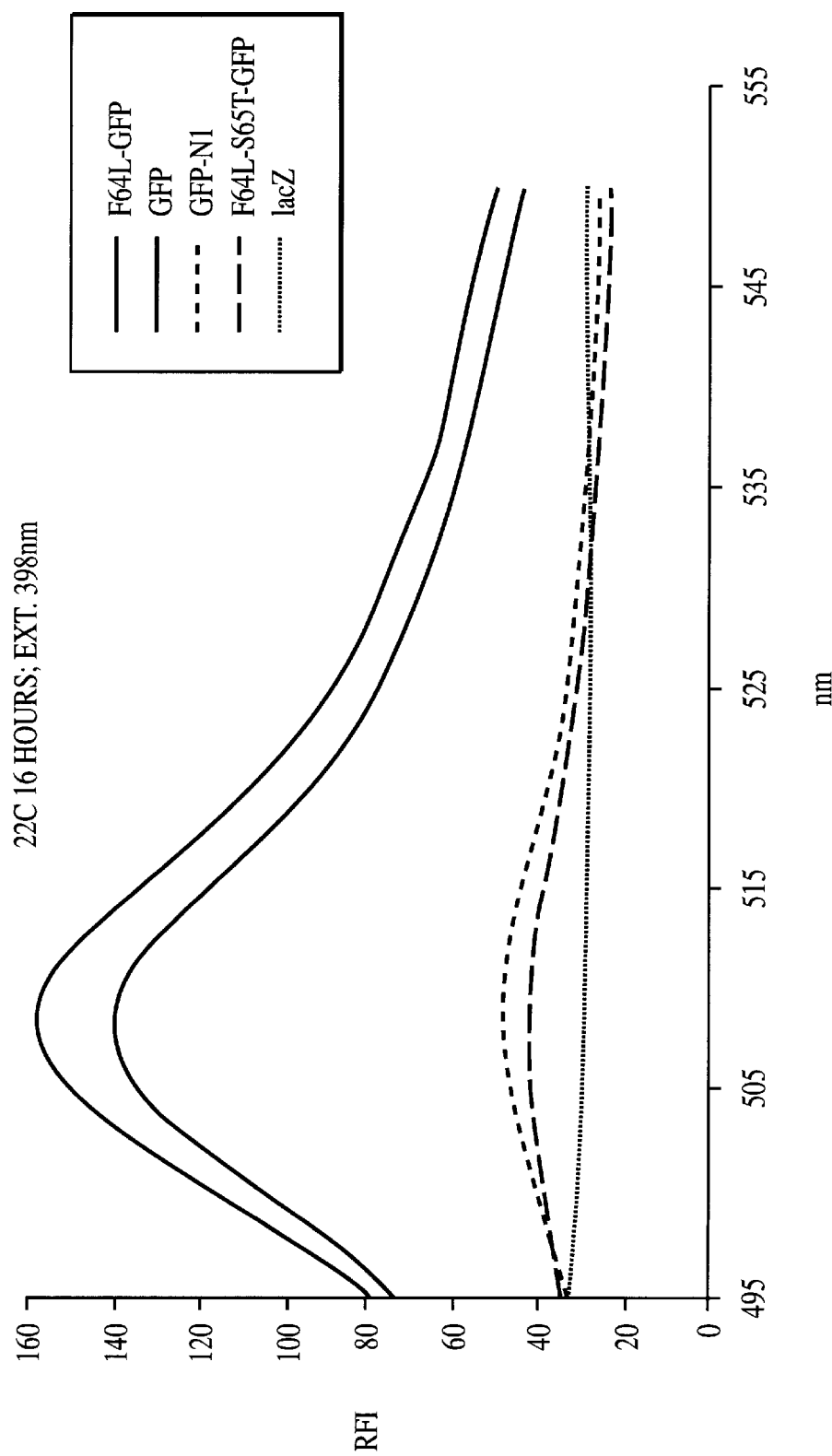
FIG. 6a is a graph of fluorescence emission spectra measured in cells grown at 22° C. for 15 hours and excited with light at 398 nm for F64L-GFP, GFP, GFP-N1, F64LS65T-GFP, and lacZ.

The results of the experiments are shown in FIGS. 6a–6f below and can be summarized as follows:

After 16 hours at 22 C using an excitation wavelength of 398 nm there were large signals for GFP and F64L-GFP, and detectable signals for GFP-N1 and F64L-S65T-GFP, cf. FIG. 6a.

Figure 6B:
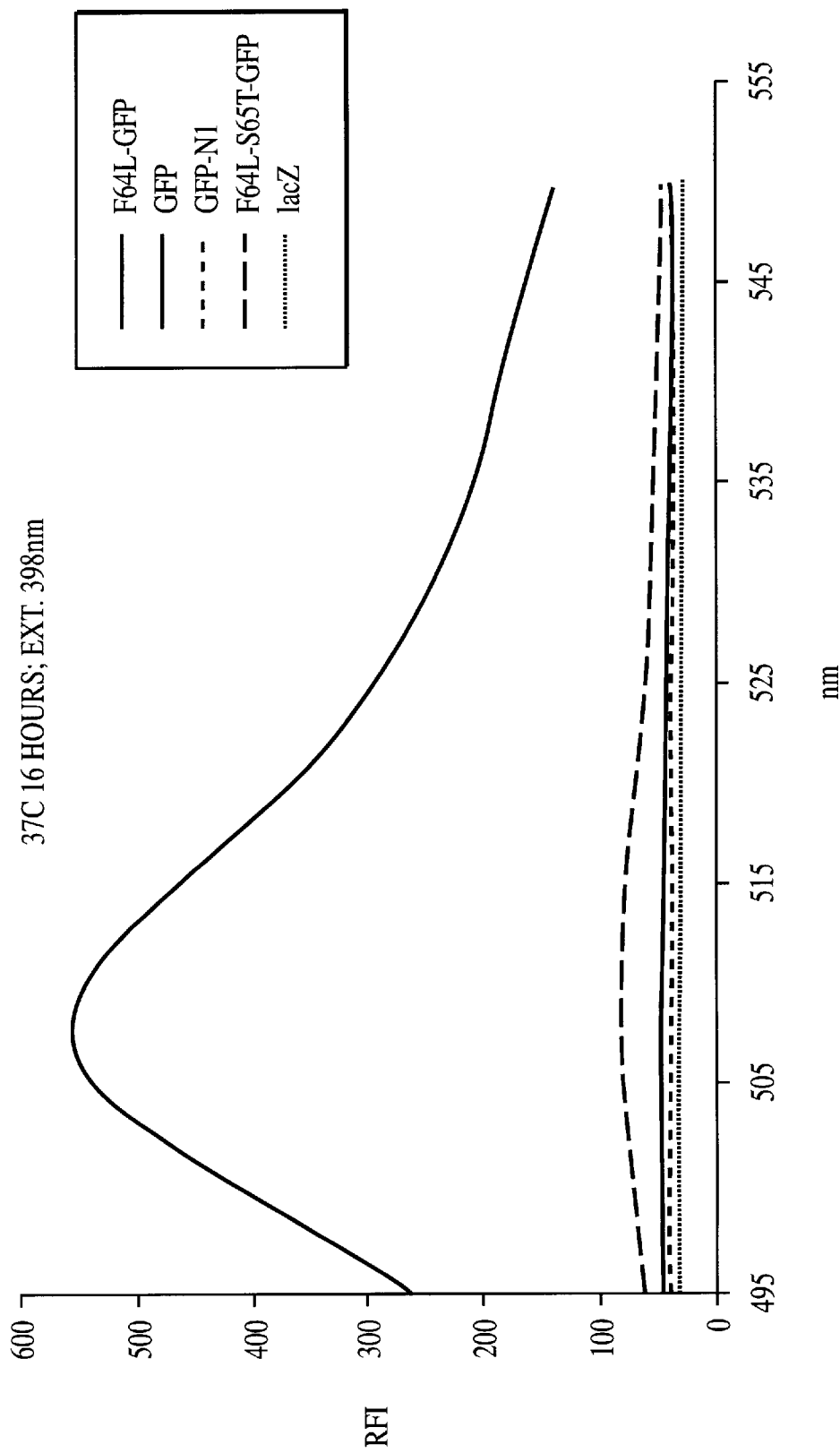
FIG. 6b is a graph of fluorescence emission spectra measured in cells grown at 37° C. for 16 hours and excited with light at 398 nm for F64L-GFP, GFP, GFP-N1, F64LS65T-GFP, and lacZ.

After 16 hours at 37 C with an excitation wavelength of 398 nm there was a large signals for F64L-GFP, a detectable signal for F64L-S65T-GFP, and no detectable signals for GFP and GFP-N1, cf. FIG. 6b.

Figure 6C:
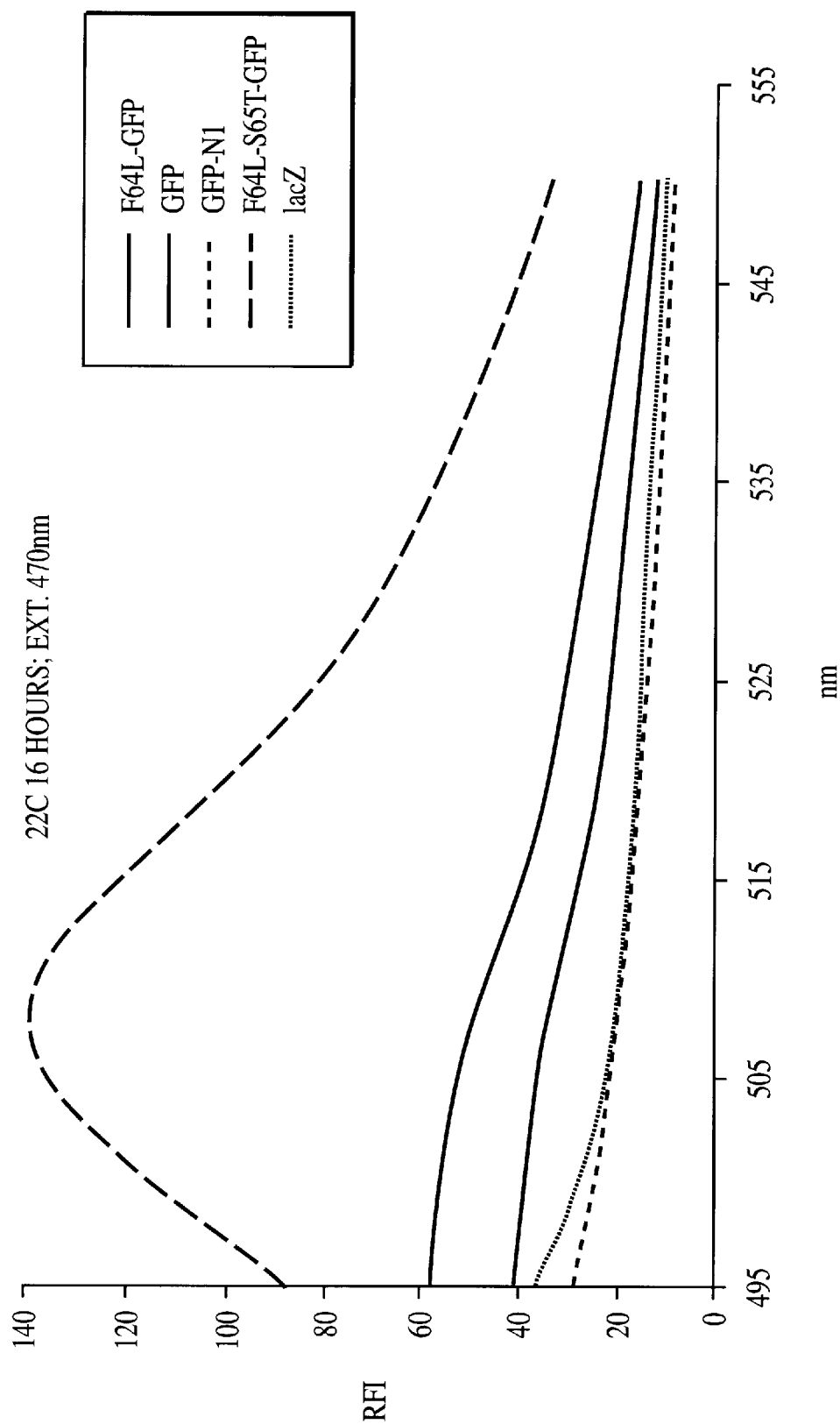
FIG. 6c is a graph of fluorescence emission spectra measured in cells grown at 22° C. for 16 hours and excited with light at 470 nm for F64L-GFP, GFP, GFP-N1, F64LS65T-GFP, and lacZ.

After 16 hours at 22 C with an excitation wavelength of 470 nm there was a large signals for F64L-S65T-GFP, detectable signals for GFP and F64L-GFP, and no detectable signals for GFP-N1, cf. FIG. 6c.

Figure 6D:
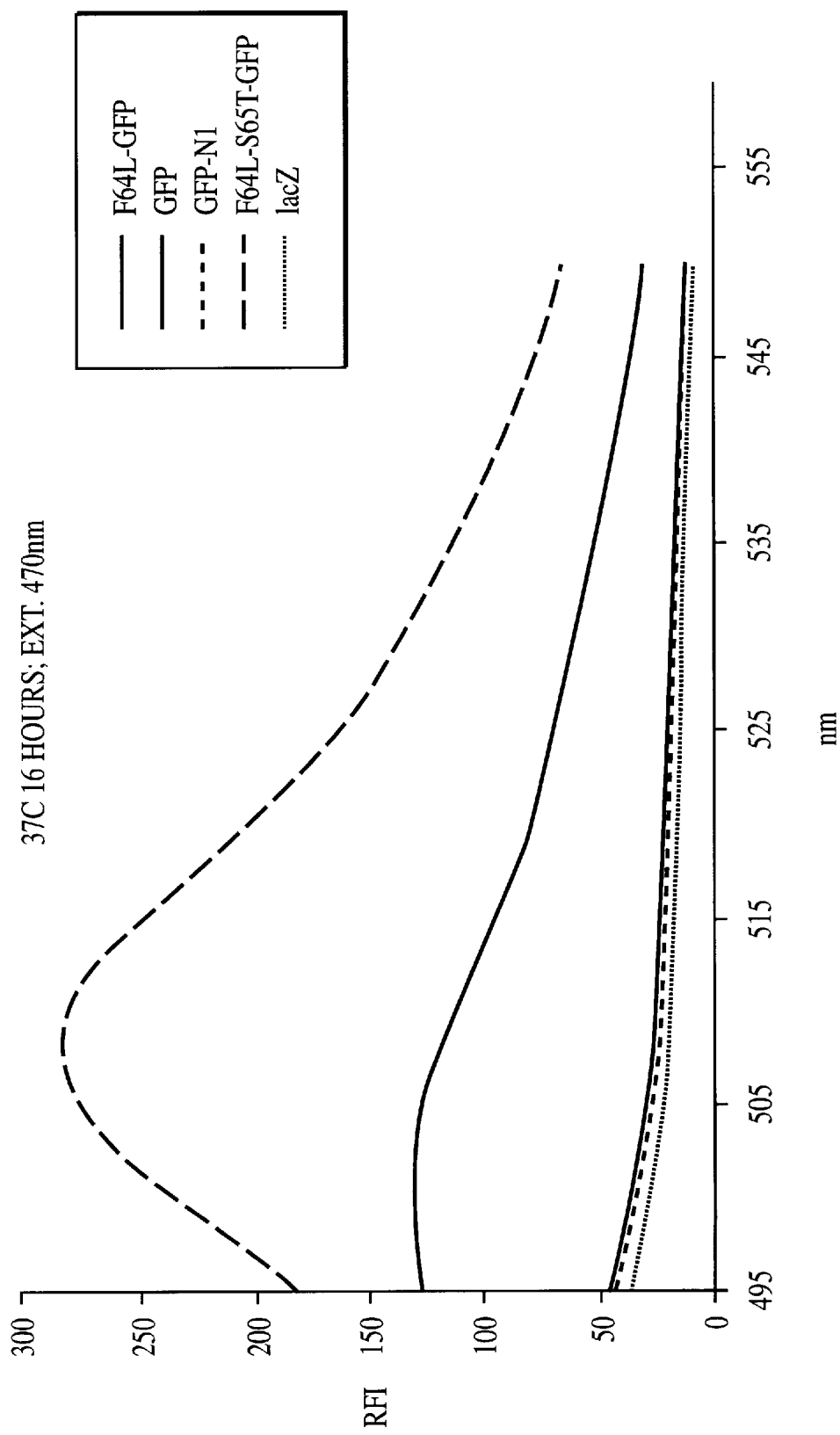
FIG. 6d is a graph of fluorescence emission spectra measured in cells grown at 37° C. for 16 hours and excited with light at 470 nm for F64L-GFP, GFP, GFP-N 1, F64LS65T-GFP, and lacZ.

After 16 hours at 37 C with an excitation wavelength of 470 nm there were large signals for F64L-S65T-GFP and F64L-GFP, and no detectable signals for GFP and GFP-N1, cf. FIG. 6d.

Figure 6E:
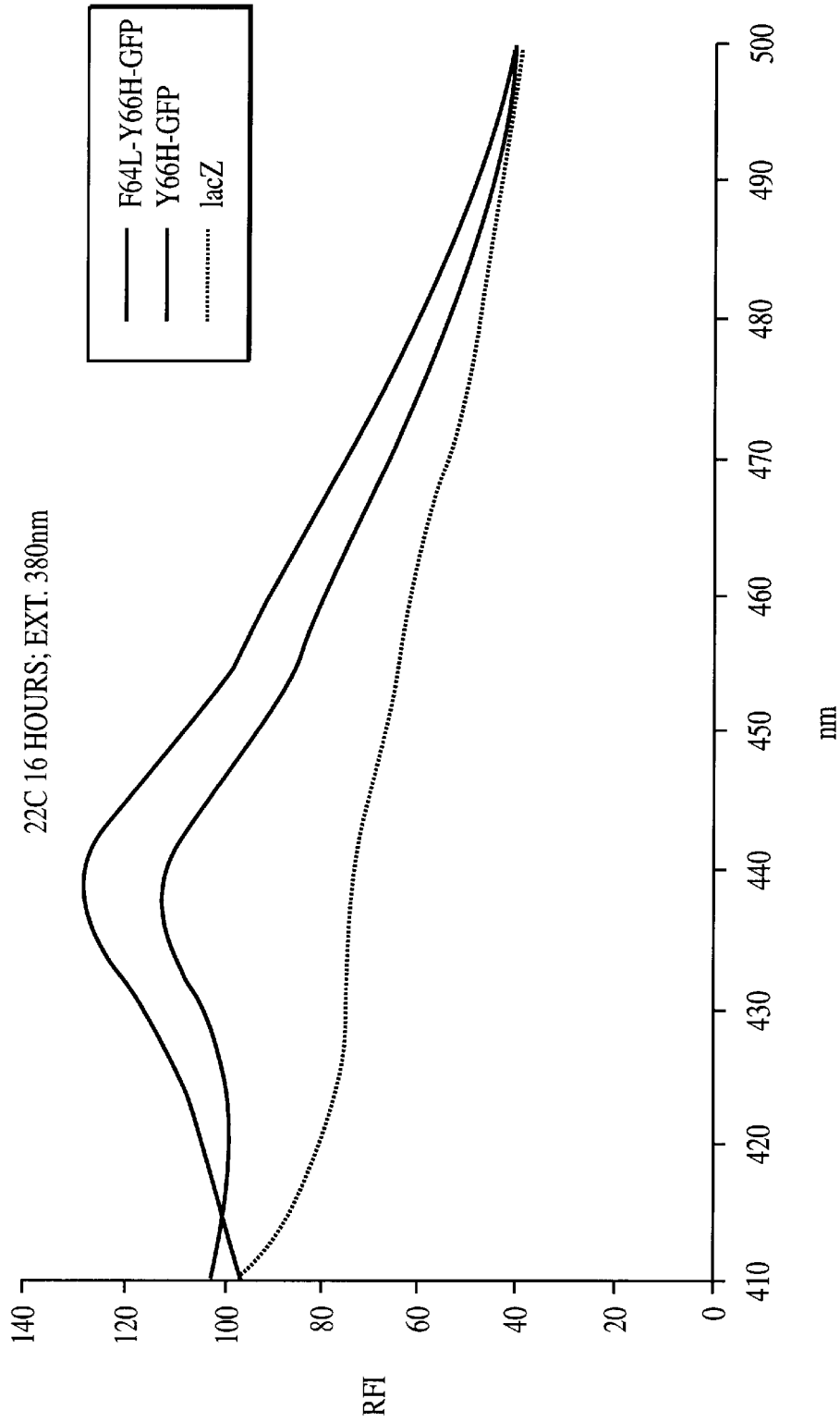
FIG. 6e is a graph of fluorescence emission spectra measured in cells grown at 22° C. for 16 hours and excited with light at 380 nm for F64L-Y66H-GFP, Y66H-GFP and lacZ.

After 16 hours at 22 C with an excitation wavelength of 380 nm there were detectable signals over background for Y66H-GFP and F64L-Y66H-GFP, cf. FIG. 6e.

Figure 6F:
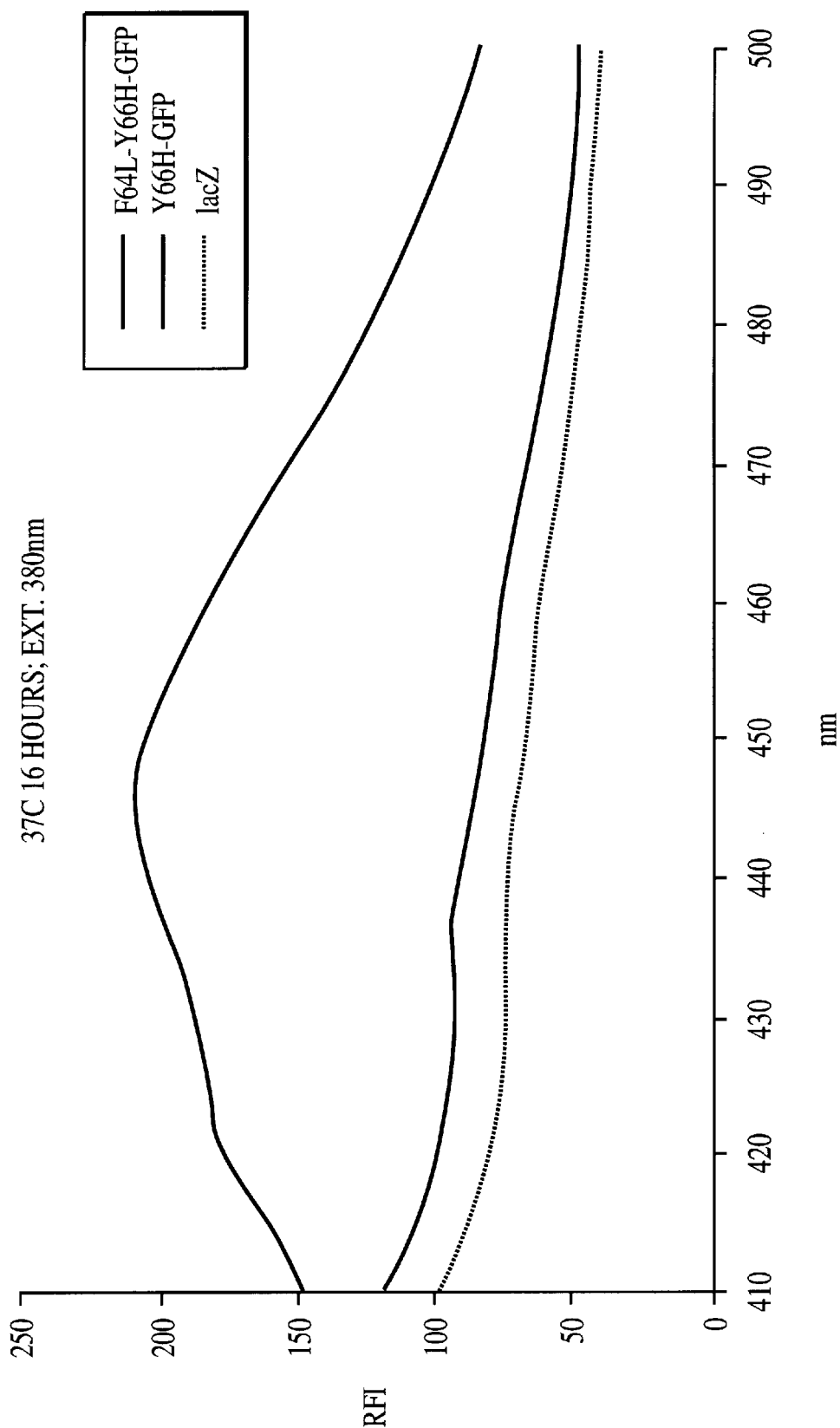
FIG. 6f is a graph of fluorescence emission spectra measured in cells grown at 37° C. for 16 hours and excited with light at 380 nm for F64L-Y66H-GFP, Y66H-GFP and lacZ.

After 16 hours at 37 C with an excitation wavelength of 380 nm there was no detectable signal over background for Y66H-GFP and a large signal for F64L-Y66HGFP, cf. FIG. 6f.

To determine whether the differences in fluorescence signals were due to differences in expression levels, total protein from the E.coli cells (0.5 OD$_{450}$ units) analyzed as described above was fractionated by SDS-polyacrylamide gel electrophoresis (12% Tris-glycine gels from BIO-RAD Laboratories) followed by Western blot analysis (ECL Western blotting from Amersham International) with polyclonal GFP antibodies (from rabbit). The result showed that expression levels of GFP, GFP-N1, F64L-GFP, F64L-S65T-GFP, Y66H-GFP and F64L-Y66H-GFP were identical, both at 22 C and 37 C. The differences in fluorescence signals are therefore not due to different expression levels.

EXAMPLE 3

Influence of the F64L substitution on GFP and its derivatives when expressed in mammalian cells.

F64L-Y66H-GFP, F64L-GFP, and F64L-S65T-GFP were cloned into pcDNA3 (Invitrogen, Calif., USA) so that the expression was under control of the CMV promoter. Wild-type GFP was expressed from the pGFP-N1 plasmid (Clontech, Calif., USA) in which the CMV promoter controls the expression. Plasmid DNA to be used for transfection were purified using Jetstar Plasmid kit (Genomed Inc. N.C., USA) and was dissolved in distilled water.

The precipitate used for the transfections were made by mixing the following components: 2 µg DNA in 44 µl of water were mixed with 50 µl 2× HBS buffer (280 mM NaCl, 1.5 mM Na$_2$HPO$_4$, 12 mM dextrose, 50 mM HEPES) and 6.2 µl 2M CaCl$_2$. The transfection mix was incubated at room temperature for 25 minutes before it was added to the cells. HEK 293 cells (ATCC CRL 1573) were grown in 2 cm by 2 cm coverglass chambers (Nunc, Denmark) with approximately 1.5 ml medium (Dulbecco's MEM with glutamax-1, 4500 mg/L glucose, and 10% FCS; Gibco BRL, MD, USA). The DNA was added to cells at 25–50% confluence. Cells were grown at 37° C. in a CO$_2$ incubator. Prior to visualisation the medium was removed and 1.5 ml Ca$^{2+}$-HEPES buffer (5 mM KCl, 140 mM NaCl, 5.5 mM glucose, 1 mM MgSO$_4$, 1 mM CaCl, 10 mM HEPES) was added to the chamber.

Transfectants were visualised using an Axiovert 135 (Carl Zeiss, Germany) fluorescence microscope. The microscope was equipped with an HBO 100 mercury excitation source and a 40×, Fluar, NA=1.3 objective (Carl Zeiss, Germany). To visualise GFP, F64L-GFP, and F64L-S65T-GFP the following filters were used: excitation 480/40 nm, dichroic 505 nm, and emission 510LP nm (all from Chroma Technologies Corp., Vt., USA). To visualise F64L-Y66H-GFP the following filters were used: excitation 380/15 nm, dichroic 400 run, and emission 450/65 nm (all from Omega Optical, Vt., USA).

Cells in several chambers were transfected in parallel, so that, a new chamber could be taken for each sample point. In cases where the incubation extended beyond 8.5 hours the Ca$^{2+}$ precipitate was removed by replacing the medium.

As shown in Table 1 the F64L mutation enhances the fluorescent signal significantly (wild type GFP versus F64L-GFP and F64L-S65T-GFP). Fluorescent cells can be observed as early as 1–2 hours post-transfection indicating an efficient maturation of the chromophore at 37° C. Furthermore, the F64L mutation is enhancing other GFP derivatives like the S65T mutant which has a shifted excitation spectrum and the blue derivative which is not detectable in mammalian cells without the F64L substitution. (Comment: When comparing the results of F64L-S65T-GFP and F64L-GFP one has to take into account that the excitation spectra differ and that the filter set used is optimised for F64L-S65T-GFP. F64L-GFP and WT GFP share the same spectral properties.)

What is claimed is:

1. A Green Fluorescent Protein (GFP) polypeptide that has the amino acid sequence of SEQ ID NO:22 with the exception that a Leu residue is substituted for the Phe residue at position 64 of SEQ ID NO:22 wherein said substituted GFP exhibits increased fluorescence at a temperature of 30° or above, relative to the GFP that has the amino acid sequence of SEQ ID NO:22, when expressed in a host cell.

2. The substituted GFP of claim 1, wherein said substituted GFP is produced by substituting said Leu residue into the amino acid sequence of SEQ ID NO:22 which is isolated from Aequorea victoria or Renilla reniformis.

3. The substituted GFP of claim 1, wherein the substituted GFP exhibits increased fluorescence at about 37° relative to the GFP that has the amino acid sequence of SEQ ID NO:22.

4. A Green Fluorescent Protein (GFP) polypeptide that has the amino acid sequence of SEQ ID NO:22 with the exception that a Ile residue is substituted for the Phe residue at position 64 of SEQ ID NO:22 wherein said substituted GFP exhibits increased fluorescence at a temperature of 30° or above, relative to the GFP that has the amino acid sequence of SEQ ID NO:22, when expressed in a host cell.

5. A Green Fluorescent Protein (GFP) polypeptide that has the amino acid sequence of SEQ ID NO:22 with the exception that a Val residue is substituted for the Phe residue at position 64 of SEQ ID NO:22 wherein said substituted GFP exhibits increased fluorescence at a temperature of 30° or above, relative to the GFP that has the amino acid sequence of SEQ ID NO:22, when expressed in a host cell.

6. A Green Fluorescent Protein (GFP) polypeptide that has the amino acid sequence of SEQ ID NO:22 with the exception that a Ala residue is substituted for the Phe residue at position 64 of SEQ ID NO:22 wherein said substituted GFP exhibits increased fluorescence at a temperature of 30° or above, relative to the GFP that has the amino acid sequence of SEQ ID NO:22, when expressed in a host cell.

7. A Green Fluorescent Protein (GFP) polypeptide that has the amino acid sequence of SEQ ID NO:22 with the exception that an amino acid residue selected from the group consisting of Leu, Ile, Val, Gly and Ala is substituted for the Phe residue at position 64 of SEQ ID NO:22 wherein said substituted GFP exhibits increased fluorescence at a temperature of 30° or above, relative to the GFP that has the amino acid sequence of SEQ ID NO:22, when expressed in a host cell.

8. The substituted Green Fluorescent Protein (GFP) polypeptide of claim 7 wherein a Leu residue is substituted for the Phe residue at position 64 of SEQ ID NO:22 which is further substituted in that a His residue is substituted for the Tyr residue at position 66 of SEQ ID NO:22.

9. The substituted Green Fluorescent Protein (GFP) polypeptide of claim 7 wherein a Ile residue is substituted for the Phe residue at position 64 of SEQ ID NO:22 which is further substituted in that a His residue is substituted for the Tyr residue at position 66 of SEQ ID NO:22.

10. The substituted Green Fluorescent Protein (GFP) polypeptide of claim 7 wherein a Ala residue is substituted for the Phe residue at position 64 of SEQ ID NO:22 which is further substituted in that a His residue is substituted for the Tyr residue at position 66 of SEQ ID NO:22.

11. The substituted Green Fluorescent Protein (GFP) polypeptide of claim 7 wherein a Val residue is substituted for the Phe residue at position 64 of SEQ ID NO:22 which is further substituted in that a His residue is substituted for the Tyr residue at position 66 of SEQ ID NO:22.

12. The substituted Green Fluorescent Protein (GFP) polypeptide of claim 7 wherein a Gly residue is substituted for the Phe residue at position 64 of SEQ ID NO:22 which is further substituted in that a His residue is substituted for the Tyr residue at position 66 of SEQ ID NO:22.

13. A Green Fluorescent Protein (GFP) having the amino acid sequence of SEQ ID NO: 16.

14. A Green Fluorescent Protein (GFP) having the amino acid sequence of SEQ ID NO: 18.

15. A Green Fluorescent Protein (GFP) having the amino acid sequence of SEQ ID NO:20.

* * * * *